(12) United States Patent
Fitzgerald et al.

(10) Patent No.: US 8,323,330 B2
(45) Date of Patent: Dec. 4, 2012

(54) STENT WITH COMPACT CRIMP CONFIGURATION

(75) Inventors: Keif Fitzgerald, San Jose, CA (US); Boris Anukhin, San Jose, CA (US)

(73) Assignee: Abbott Cardiovascular Systems Inc., Santa Clara, CA (US)

(*) Notice: Subject to any disclaimer, the term of this patent is extended or adjusted under 35 U.S.C. 154(b) by 160 days.

(21) Appl. No.: 12/820,694

(22) Filed: Jun. 22, 2010

(65) Prior Publication Data
US 2011/0313509 A1  Dec. 22, 2011

(51) Int. Cl.
A61F 2/06    (2006.01)
(52) U.S. Cl. ............................... 623/1.16; 623/1.15

(58) Field of Classification Search ............... 623/1.15, 623/1.16, 1.2, 1.44
See application file for complete search history.

(56) References Cited

U.S. PATENT DOCUMENTS
2007/0055348 A1 * 3/2007 Pryor ..................... 623/1.15
* cited by examiner Primary Examiner — Christopher D Koharski
Assistant Examiner — Matthew Schall
(74) Attorney, Agent, or Firm — Fulwider Patton LLP

(57) ABSTRACT

A stent having a compacted configuration in which adjacent crowns of its undulating rings overlap one another. The overlapping compacted configuration provides for a relatively low profile in view of the coverage that is achieved by the stent upon expansion.

6 Claims, 3 Drawing Sheets

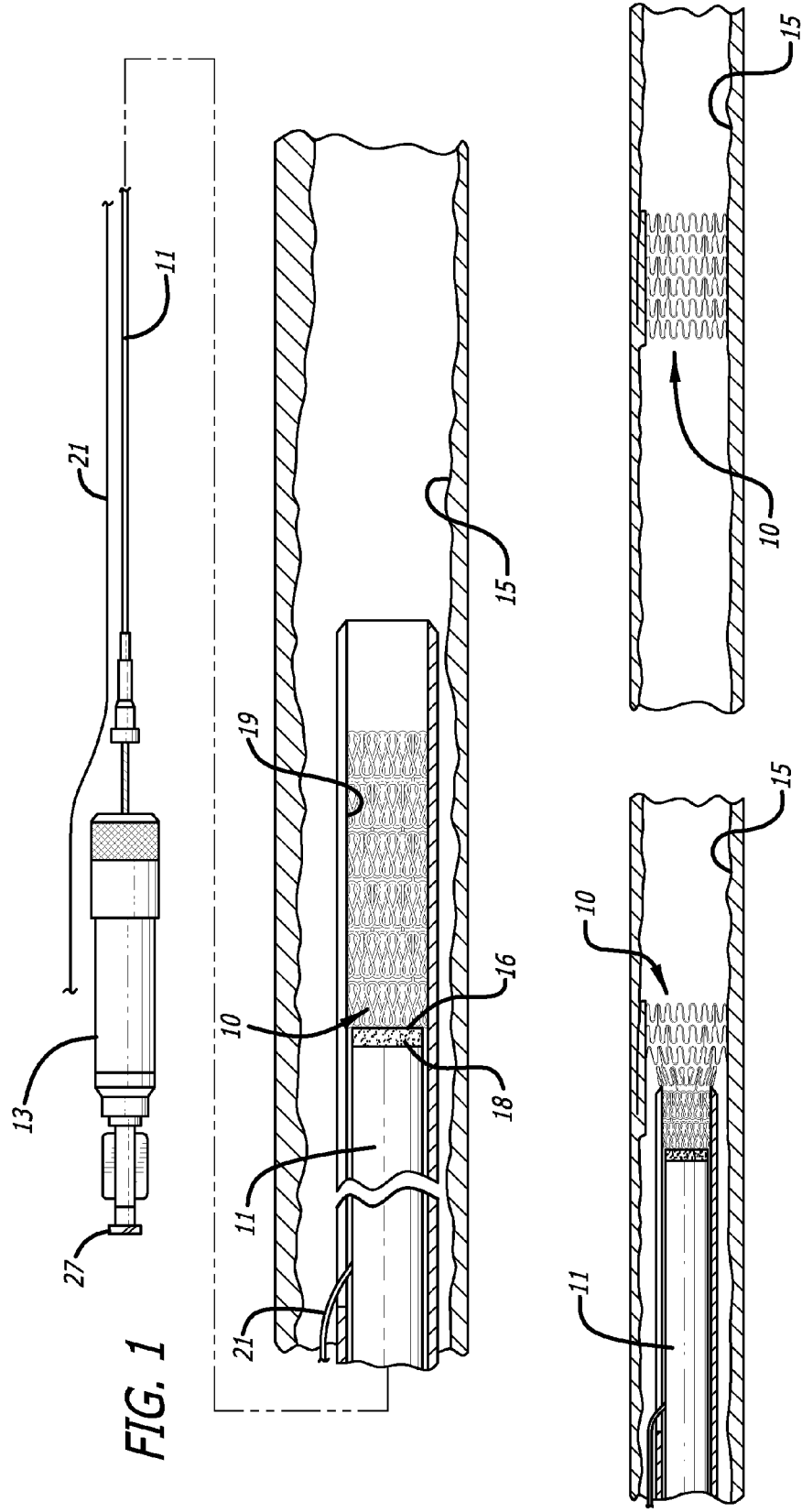

STENT WITH COMPACT CRIMP CONFIGURATION

The present invention is generally directed to an expandable arterial stent, and more particularly pertains to a stent configured for a low profile while in a crimped state.

BACKGROUND

Stents are generally cylindrically-shaped devices that function to hold open and sometimes expand a segment of a blood vessel or other lumen such as a coronary artery. They are particularly suitable for use to support the lumen or hold back a dissected arterial lining which can occlude the fluid passageway therethrough. A stent is introduced into a patient's vasculature and advanced to the deployment site in a collapsed state. Once in position, the stent is allowed to expand so as to engage the vessel walls.

In order to facilitate the stent's introduction into a patient's vasculature and its advancement therethrough, it is desirable for the stent to have as minimal a profile as possible while in its collapsed state. Conversely, the stent should preferably provide as much coverage of the vessel walls as possible while in its expanded state. These seemingly conflicting design parameters have heretofore been addressed with the use of stent patterns that represent trade-offs. Accordingly, some stent patterns serve to minimize cross-section of the stent in its collapsed state while others serve to maximize coverage of the stent while in its expanded state. A stent configuration is needed that provides for a greater spread between its profile while in the collapsed condition and its coverage in the expanded condition than has heretofore been possible.

Some stents are designed to be self expanding and open without a balloon catheter. In these cases, the stent is enclosed in a sheath on the catheter and positioned inside the patient's vascular. The sheath can be retracted when the catheter end is at the designated location, pushing the stent out to expand upon release from the sheath. In this situation, the size of the sheath that covers the stent in its collapsed state is an important factor in the overall profile of the working portion of the device. The inner diameter of the sheath is limited by the diameter of the self-expanding stent in its collapsed state. For many current stent designs, the collapsed diameter is defined by the width of a crown multiplied by the number of crowns, divided by $\pi$. If the diameter of the stent could be reduced in the collapsed state, a smaller sheath diameter could be employed reducing the overall profile of the device.

SUMMARY OF THE INVENTION

The present invention provides for a stent configuration that maximizes coverage while in its expanded state yet exhibits a low profile while in its compact state. This is achieved with a stent pattern that facilitates the overlapping of adjacent crowns so that the empty volume of the stent's interior can be utilized, reducing the overall stent diameter.

In accordance with the present invention the stent is comprised of a series of undulating rings that are linked to one another along a common axis. The undulations permit each ring to expand during deployment of the stent and each ring consists of a series of crowns that are interconnected by struts. Each ring of the stent includes a large number of undulations in order to enhance coverage (i.e. the total area of stent structure that contacts walls of the vessel in which it is deployed). In order to avoid interference between adjacent undulations in the compressed state, and more particularly, in order to avoid interference between the crowns of adjacent undulations, the crowns in the stent of the present invention assume an overlapping pattern. Adjacent crowns alternate between a position outside and a position inside the nominal circumferential plane defined by the stent. This overlapping configuration accomplishes a smaller crimped profile for a given amount of coverage. Conversely, more coverage is achievable for a given crimped profile.

These and other features and advantages of the present invention will become apparent from the following detailed description of the preferred embodiments which, taken in conjunction with the accompanying drawings, illustrate by way of example the principles of the present invention.

BRIEF DESCRIPTION OF THE DRAWINGS

FIG. 1 is an enlarged view, partially in section, of a stent embodying features of the invention which is secured in a delivery catheter;

FIG. 2 is an enlarged view, partially in section, similar to that shown in FIG. 1, wherein the stent is partially pushed out of the catheter into the body lumen;

FIG. 3 is an enlarged view showing the expanded stent in place within the body lumen after delivery by the catheter;

DETAILED DESCRIPTION OF THE PREFERRED EMBODIMENTS

Figure 4:
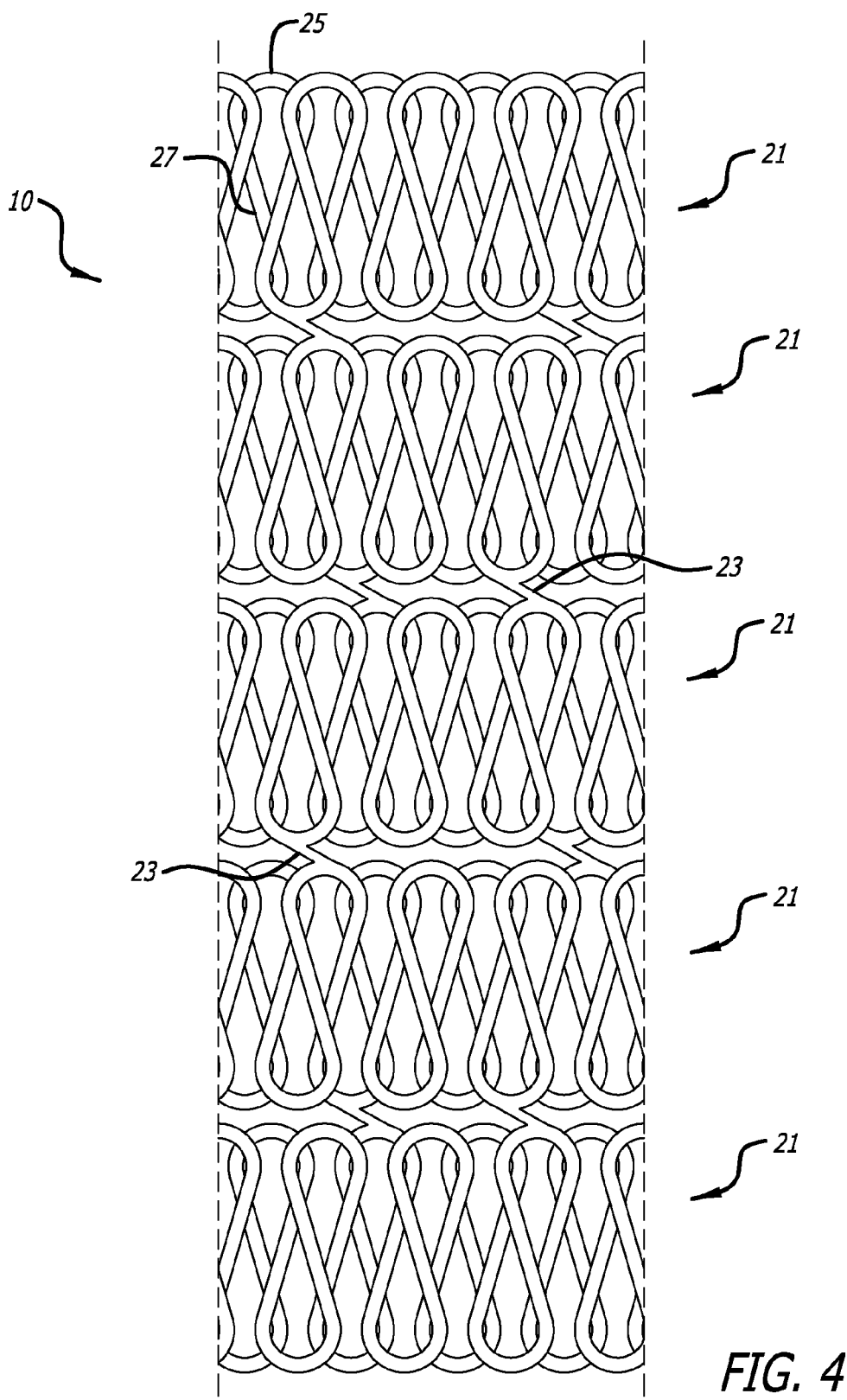
FIG. 4 is a plan view of a section of a longitudinally dissected and flattened portion of the stent of the present invention while in a compacted state.

Referring now to the drawings, and particularly FIG. 1, there is shown a stent 10 that is mounted onto a delivery catheter 11. The stent is a precisely patterned tubular device that is expandable. The stent has two states, an expanded state and a compacted state. In FIG. 1, the stent is in the compacted state, enclosed in a sheath 19 that maintains the stent 10 in its delivery position with a reduced profile to facilitate the assembly's advancement through the patient's vasculature.

The delivery of the stent 10 is accomplished in the following manner: the stent 10 is first placed into the catheter's sleeve 19 distal to an inner member 16 of the delivery catheter 11 in a crimped or collapsed state, such as that shown in FIG. 1. The inner member 16 may be equipped with a radiopaque marker 18 to help position the stent as is known in the art. The catheter-stent assembly is introduced into the patient's vasculature through, for example, a guiding catheter (not shown). A guide wire 21 is advanced across the target arterial section and then the catheter/stent assembly is advanced over the guide wire within the artery 15 until the stent 10 is positioned in the target area using the radiopaque marker for guidance on a fluoroscope or other apparatus. If the stent is a self-expanding stent, an actuator 27 on the handle 13 may be actuated to withdraw the sheath 19 so that the stent 10 bears against inner member 16 as the sheath is withdrawn, releasing and deploying the stent at a predetermined site in a body lumen 15. Such a stent delivery system is disclosed in U.S. Pat. No. 7,175,650, issued Feb. 13, 2007 to Ruetsch, the contents and disclosures of which are fully incorporated herein by reference. The stent 10 in FIG. 2 is shown partially expelled from the catheter 11 as the sheath 19 is withdrawn, allowing the self-expanding stent 10 to attain a diameter that matches the interior dimension of the body lumen 15. Alternatively, the stent 10 can be mounted on a balloon (not shown) if the stent is not self-expanding, and as the balloon is inflated, it expands the stent against the artery, as is well known in the art. After the stent 10 expands, it retains its expanded shape due to the interlocking elements as is well known in the art.

The stent 10 in its expanded state serves to hold open the artery 15 after the catheter 11 is withdrawn, as illustrated in FIG. 3. The stent 10 will eventually become covered with endothelial cell growth which minimizes blood flow interference. The closely spaced elements of the stent provide uniform support for the wall of the artery and, consequently, are well adapted to tack up and hold in place small flaps or dissection in the wall of the artery.

Figure 5:
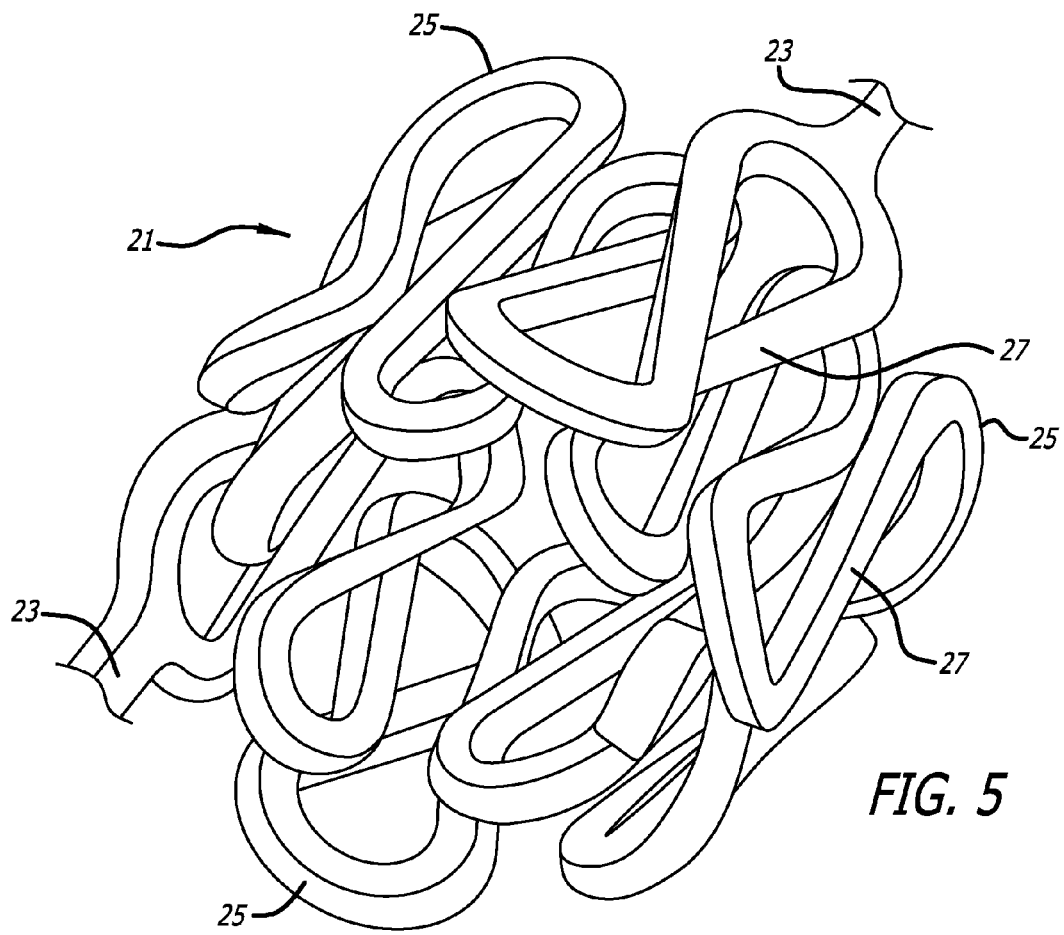
FIG. 5 is an enlarged, elevated perspective view of a single ring of a stent of the present invention in its compacted state illustrating the overlapping pattern.
Figure 6:
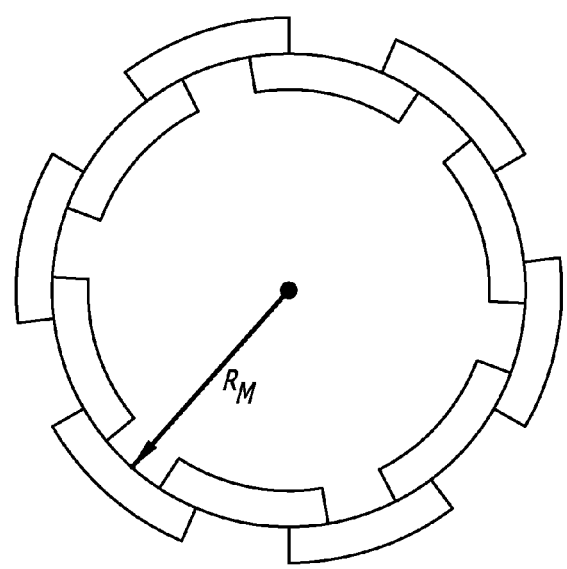
FIG. 6 shows the stent of FIG. 5 looking through the stent.

FIG. 4 is plan view of the stent 10, longitudinally dissected, flattened and partially in section, in its compacted state. The stent 10 consists of plurality of undulating rings 21 that are interconnected by links 23. The undulations are defined by crowns 25 and struts 27 that extend between the crowns. It can be seen that the crowns 25 alternate between "over" and "under" in an alternating manner that allows a partial stacking of the ring. Overlapping the widest part of the ring, i.e. the crown 25, reduces the overall effective circumference of the stent 10 in the compacted state, but does not affect the coverage of the stent in the expanded state. FIGS. 5 and 6 are perspective and axial views of a single undulating ring 21 in its compacted state. Adjacent crowns 25 overlap one another such that the crowns alternately extend inside and outside the nominal cylindrical plane, or mean circumference, defined generally by the midpoint of the ring or by connecting midpoints of the links. As a result, the stent's overall outer diameter is reduced as compared with a stent without the overlapping pattern as interference between adjacent crowns is avoided leading to a more compact or tight configuration.

If only two crown elevations are desired (i.e., two layers of overlap), the most compact configuration occurs when the alternating crowns come in contact with each other on the "inner" ring. The outer ring will not have the crowns touching in this configuration because the same number of crowns must fill a bigger circle, leading to small gaps between the crowns of the outer layer. To achieve an even higher ratio of compactness, the stents can be configured so that the crowns 25 along each end of the rings are stacked in more than two radial positions, i.e. three layers or more. This causes move material to fill the otherwise hollow area inside the stent, leading to a more compact stent.

In the case of the self-expanding sheath, the inner diameter of the sheath 19 is limited by the outer diameter of the collapsed stent 10. In the present invention, due to the overlapping nature of the stents crowns in the compacted state, the diameter of the stent can be reduced in a two layer configuration with the crowns on the inner layer touching such that it is the width of the crowns multiplied by the number of crowns (i.e., the circumference of the inner layer), divided by 2 (because the two layers reduces the number of crowns that form the inner layer by 2), divided by $\pi$ (the formula for determining a diameter of a circle from a circumference), plus the thickness of the stent×2 (the additional diameter width due to the material of the overlapping outer layer on each side of the inner layer). With higher orders of overlapping layers, an even smaller diameter can be achieved. This reduction in the diameter represents a significant improvement over the prior designs.

The stent 10 of the present invention can be made in many ways. One method of making the stent is to cut a thin-walled tubular member, such as stainless steel tubing to remove portions of the tubing in the desired pattern for the stent, leaving relatively untouched the portions of the metallic tubing which are to form the stent. The stent also can be made from other metal alloys such as tantalum, nickel-titanium, cobalt-chromium, titanium, shape memory and superelastic alloys, and the Nobel metals such as gold or platinum. In accordance with the invention, it is preferred to cut the tubing in the desired pattern by means of a machine-controlled laser as is well known in the art.

The stent of the present invention also can be made from metal alloys other than stainless steel, such as shape memory alloys. Shape memory alloys are well known and include, but are not limited to, nickel-titanium and nickel-titanium-vanadium. Any of the shape memory alloys can be formed into a tube and laser cut in order to form the pattern of the stent of the present invention. As is well known, the shape memory alloys of the stent of the present invention can include the type having superelastic or thermoelastic martensitic transformation, or display stress-induced martensite. These types of alloys are well known in the art and need not be further described here. Importantly, a stent formed of shape memory alloys, whether the thermoelastic or the stress-induced martensite-type, can be delivered using a balloon catheter of the type described herein, or be delivered via a catheter without a balloon or a sheath catheter.

The present invention stent is ideally suited, for example, for drug delivery (i.e., delivery of a therapeutic agent) since it has a uniform surface area which ensures uniform distribution of drugs. Typically, a polymer is coated onto the stent of the type disclosed in U.S. Pat. Nos. 6,824,559 and 6,783,793 which are incorporated herein by reference. These bioactive agents can be any agent, which is a therapeutic, prophylactic, or diagnostic agent. These agents can have anti-proliferative or anti-inflammmatory properties or can have other properties such as antineoplastic, antiplatelet, anti-coagulant, anti-fibrin, antithrombonic, antimitotic, antibiotic, antiallergic, antioxidant as well as cytostatic agents. Representative embodiments of the active component include actinomycin D (available from Sigma-Aldrich; or Cosmegen® available from Merck) or derivatives, analogs or synonyms thereof, such as dactinomycin, actinomycin IV, actinomycin I.sub.1, actinomycin X.sub.1, and actinomycin C.sub.1; podophyllotoxins such as etoposide and teniposide (Bristol Myers Squibb and Sigma Chemical); cephalotin (Bristol Myers Squibb); trapidil; ticlopidine (Danbury Pharma, Genpharm); tranilast (SmithKline Beecham and LG Chemical Kissei, Japan); IIb-IIIa inhibitors such as eptifibatide (COR therapeutic); clobetasol (Glaxo Wellcome); COX-2 inhibitors such as celecoxib (CELEBREX) (Searle and Pfizer) and rofecoxib (VIOXX) (Merck); PGE1 or alprostadil (Bedford); bleomycin; ENDOSTATIN (EntreMed); ANGIOSTATIN (EntreMed); thalidomide; 2-methoxyestraidol (EntreMed and Sigma Chemical) curcimin (the major constituent of turmeric power extract from the rhizomes of the plant *Curcuma longa* L found in south and southeast tropical Asia); cisplatin (Sigma Chemical); dipyridamole; tirofiban; verapamil; vitronectine; argatroban; and carboplatin (Sigma Chemical). Additionally corticosteroids such as anti-inflammatory glucocorticoids including clobetasol, diflucortolone, flucinolone, halcinonide, and halobetasol can also be used.

In one embodiment, faster acting non-steroidal anti-inflammatory agents such as naproxen, aspirin, ibuprofen, fenoprofin, indomethacin, and phenylbutazone can be used in conjunction with the glucocorticoids. The use of a non-steroidal anti-inflammatory agent is useful during the early stages of the inflammation in response to a mechanically mediated vascular injury. Examples of suitable therapeutic and prophylactic agents include synthetic inorganic and organic compounds, proteins and peptides, polysaccharides and other sugars, lipids, and DNA and RNA nucleic acid sequences having therapeutic, prophylactic or diagnostic activities. Nucleic acid sequences include genes, antisense molecules which bind to complementary DNA to inhibit transcription, and ribozymes. Some other examples of other bioactive agents include antibodies, receptor ligands, enzymes, adhesion peptides, blood clotting factors, inhibitors or clot dissolving agents such as streptokinase and tissue plasminogen activator, antigens for immunization, hormones and growth factors, oligonucleotides such as antisense oligonucleotides and ribozymes and retroviral vectors for use in gene therapy. Examples of anti-proliferative agents include rapamycin and its functional or structural derivatives, 40-O-(2-hydroxy)ethyl-rapamycin (everolimus), and its functional or structural derivatives, paclitaxel and its functional and structural derivatives. Examples of rapamycin derivatives include methyl rapamycin, ABT-578, 40-O-(3-hydroxy)propyl-rapamycin, 40-O-[2-(2-hydroxy)ethoxy]ethyl-rapamycin, and 40-O-tetrazole-rapamycin. Examples of paclitaxel derivatives include docetaxel. Examples of antineoplastics and/or antimitotics include methotrexate, azathioprine, vincristine, vinblastine, fluorouracil, doxorubicin hydrochloride (e.g. Adriamycin® from Pharmacia & Upjohn, Peapack N.J.), and mitomycin (e.g. Mutamycin® from Bristol-Myers Squibb Co., Stamford, Conn.). Examples of such antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, thrombin inhibitors such as Angiomax a (Biogen, Inc., Cambridge, Mass.), calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name Mevacore® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), nitric oxide or nitric oxide donors, super oxide dismutases, super oxide dismutase mimetic, 4-amino-2,2,6,6-tetramethylpiperidine-1-oxyl (4-amino-TEMPO), estradiol, anticancer agents, dietary supplements such as various vitamins, and a combination thereof. Examples of anti-inflammatory agents including steroidal and non-steroidal anti-inflammatory agents include tacrolimus, dexamethasone, clobetasol, combinations thereof. Examples of such cytostatic substance include angiopeptin, angiotensin converting enzyme inhibitors such as captopril (e.g. Capoten® and Capozide® from Bristol-Myers Squibb Co., Stamford, Conn.), cilazapril or lisinopril (e.g. Prinivil® and Prinzide® from Merck & Co., Inc., Whitehouse Station, N.J.). An example of an antiallergic agent is permirolast potassium.

Other therapeutic substances or agents which may be appropriate include alpha-interferon, bioactive RGD, and genetically engineered epithelial cells. The foregoing substances can also be used in the form of prodrugs or co-drugs thereof. The bioactive agents also include metabolites of the foregoing substances and prodrugs of these metabolites. The foregoing substances are listed by way of example and are not meant to be limiting. Other active agents which are currently available or that may be developed in the future are equally applicable.

While a particular form of the invention has been illustrated and described, it will be apparent to those skilled in the art that various modifications can be made without departing from the spirit and scope of the invention. Accordingly, it is not intended that the invention be limited except by the appended claims.

We claim:

1. An expandable stent having a compacted configuration and an expanded configuration, comprising:
a series of undulating rings arranged about a longitudinal axis, each undulation being defined by crowns at first and second ends of each ring that are interconnected by links, and where adjacent rings are interconnected by struts, wherein adjacent crowns on the first end of a common ring alternate between a position outside a mean circumference and a position inside a mean circumference in the stent's compacted configuration and adjacent crowns on the second end of the same common ring alternate between a position outside a mean circumference and a position inside a mean circumference in the stent's compacted configuration.

2. The expandable stent of claim 1 wherein the mean circumference is defined by midpoints of the links in a common ring.

3. The expandable stent of claim 1 wherein alternating crowns at the first end of a ring come in contact with each other and alternating crowns at the second end of the same ring come in contact with each other, where the contact occurs inside the mean circumference.

4. The expandable stent of claim 1 wherein the crowns are stacked in more than two radial positions.

5. The expandable stent of claim 1 wherein the stent is self-expanding.

6. The expandable stent of claim 1 wherein a diameter of the expandable stent in the crimped configuration is approximately equal to the number of crowns around a center of the stent multiplied by a width of a crown, divided by $2\pi$, plus twice a thickness of the stent.

* * * * *